(12) United States Patent
Albach et al.

(10) Patent No.: US 6,255,530 B1
(45) Date of Patent: Jul. 3, 2001

(54) PROCESS FOR THE PREPARATION OF SIX-MEMBERED RING CARBOCYCLES

(75) Inventors: Rolf William Albach, Köln; Manfred Jautelat, Burscheid, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/255,250

(22) Filed: Feb. 22, 1999

(30) Foreign Application Priority Data

Feb. 26, 1998 (DE) .............................................. 198 07 995

(51) Int. Cl.$^7$ .................................................. C07L 209/00
(52) U.S. Cl. ........................... 564/450; 585/269; 585/270
(58) Field of Search .................................... 585/269, 270; 564/450

(56) References Cited

U.S. PATENT DOCUMENTS 5,668,293  9/1997  Forestiere et al. .................... 585/269

FOREIGN PATENT DOCUMENTS

96/17685  6/1996  (WO) .

OTHER PUBLICATIONS

J. Blum et al, Tetrahedron Lettters, (month unavailable) 1983, pp. 4139–4142, XP–002102978.
Tetrahedron Letters, vol. 24, No. 38, pp 4139–4142, 1983 (month unavailable).

*Primary Examiner*—Paul J. Killos
(74) *Attorney, Agent, or Firm*—Joseph C. Gil; Diderico van Eyl

(57) ABSTRACT

Six-membered ring carbocycles of the formula (II) can be prepared by ring hydrogenation of aromatic compounds of the formula (I)

(I)

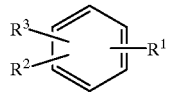

(II)

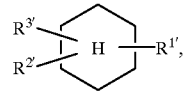

the definitions for which are given in the description, in a reaction system consisting of two liquid, immiscible phases in which elemental hydrogen is dispersed. The first phase consists of the aromatic compound (I) and, if necessary, a water-immiscible solvent. The second phase is essentially aqueous and comprises, colloidally dispersed therein, a hydrogenation-active metal as hydrogenation catalyst, and auxiliaries for stabilizing the colloidal catalyst. The process is carried out at from 50 to 180° C. and from 1 bar to 400 bar.

13 Claims, No Drawings

PROCESS FOR THE PREPARATION OF SIX-MEMBERED RING CARBOCYCLES

BACKGROUND OF THE INVENTION

The present invention relates to a process for the preparation of six-membered ring carbocycles by ring hydrogenation of aromatic compounds using hydrogen, the process being carried out in a reaction system consisting of two liquid, immiscible phases, of which the first phase is formed by the aromatic compound and, if necessary, a water-immiscible solvent, and the second phase consists of water, and, colloidally dispersed therein, a hydrogenation-active metal as hydrogenation catalyst, and auxiliaries for stabilizing the colloidal catalyst. Six-membered ring carbocycles of the type which can be prepared according to the invention are intermediates, known to the person skilled in the art, for the preparation of active ingredients and industrial chemicals.

It is already known to prepare six-membered ring carbocycles by ring hydrogenation of aromatic compounds. The hydrogenation is generally carried out using catalytically activated hydrogen; the hydrogenation-active metals suitable for this purpose are known and are generally those from the group of platinum metals and also nickel, chromium, niobium or copper. Although catalytic hydrogenations in the homogeneous phase are characterized by low diffusion inhibition, they are also characterized by the difficulty in separating the reaction product off from the reaction mixture and thus from the homogeneously dissolved catalyst by distillation, crystallization or other methods. The activity of the hydrogenation catalyst frequently also suffers at the same time. Use of slurried catalyst in the slurry phase partly overcomes the difficulty of separation although the need for coarse and fine filtration remains. There does however remain the risk of deactivating the catalyst, and a new difficulty arises, namely that of erosion in pumps, piping, valves and other parts of the apparatus by the catalyst to be removed. Difficulties of the last-mentioned type are overcome by arranging the catalyst in the form of a fixed bed in the reaction apparatus and allowing the reaction material in the liquid phase (e.g. trickle phase) or in the gas phase to flow over the catalyst. However, this reaction method, which has been perfected to a high degree, is only suitable for reactions with large throughputs. In the case of products which are prepared in small amounts and often only in batches, to carry out the reaction using catalysts in the form of a fixed bed is too complex.

DE-A 44 43 705 discloses the hydrogenation of benzene on a sulfobetaine-stabilized, colloidal catalyst comprising Ru on a $La_2O_3$ support to give cyclohexane; at 50 bar and 150° C., only 8.5% conversion and 78.5% selectivity were achieved in 0.5 h. According to Tetrahedron Letters 1983, 4139–42, the hydrogenation results deteriorate severely in the case of substituted benzenes. WO 96/08462 discloses the catalytic hydrogenation of aromatic amines to cyclohexylamines using hydrogen on an $Ru/Al_2O_3$ catalyst in the presence of LiOH, which is said to prevent deamination; the reaction medium is a water-containing water-miscible organic solvent.

SUMMARY OF THE INVENTION

It has now been found that it is possible to prepare six-membered ring carbocycles by ring hydrogenation of the corresponding aromatic compounds using a catalyst arranged in a different phase, the reaction mixture on the one hand and the hydrogenation catalyst in colloidal form on the other hand being arranged in two immiscible liquid phases. The process according to the invention is highly suitable for carrying out ring hydrogenations of aromatic compounds batchwise, although it can also be carried out continuously in a mixer/settler procedure known to the person skilled in the art.

DETAILED DESCRIPTION OF THE INVENTION

The invention relates to a process for the preparation of six-membered ring carbocycles of the formula (II) by ring hydrogenation of aromatic compounds of the formula (I)

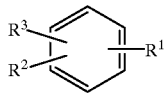
(I)

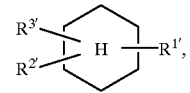
(II)

where, in the formulae, $R^1$, $R^2$ and $R^3$ independently of one another are hydrogen, straight-chain or branched $C_1$–$C_{18}$-alkyl, straight-chain or branched $C_2$–$C_{18}$-alkenyl, $C_3$–$C_8$-cycloalkyl, straight-chain or branched $C_1$–$C_{18}$-alkoxy, amino, nitro, hydroxyl, fluoro, cyano, —($C_0$–$C_4$-alkanediyl)-COO—($C_0$–$C_4$-alkyl), —($C_2$–$C_4$-alkenediyl)-COO—($C_0$–$C_4$-alkyl), —($C_0$–$C_4$-alkanediyl)-$C_6$–$C_{12}$-aryl), —O—CO—($C_1$–$C_{18}$-alkyl), —O—($C_6$–$C_{12}$-aryl), —CO—($C_1$–$C_{18}$-alkyl), —CO—($C_6$–$C_{12}$-aryl), —S—($C_6$–$C_{12}$-aryl), —NH—($C_1$–$C_{18}$-alkyl), —N($C_1$–$C_{18}$-alkyl)($C_1$–$C_4$-alkyl), —NH—($C_6$–$C_{12}$-aryl), —N($C_6$–$C_{12}$-aryl)($C_1$–$C_4$-alkyl) or —P(X)$_m$(Y)$_n$(Z)$_q$ (=O)$_r$, where X, Y and Z independently of one another are phenyl or $C_1$–$C_4$-alkyl, and Y and Z additionally and independently of one another may be $OR^4$ or $NR^4_2$, where $R^4$ is phenyl, $C_1$–$C_4$-alkoxy or $C_1$–$C_4$-alkyl, and $NR^4_2$ can also be piperidino, and Y and Z together can also be —O—$CH_2CH_2$—O—, and the bracketed term represents double-bonded oxygen, m is zero, one or two, and n, q and r independently of one another are zero or one, the sum m+n+q+r corresponding to the valency of phosphorus, where aryl constituents may be mono- or disubstituted by $C_1$–$C_4$-alkyl, $C_1$–$C_4$-alkoxy, amino, nitro, hydroxyl or mixtures thereof, and where in addition two of the radicals $R^1$, $R^2$ and $R^3$, if they are adjacent, can together be the radical of a fused benzene or 1,2-naphthalene or 2,3-naphthalene system, trimethylene, tetramethylene or propenediyl, each of which may be substituted like the aryl constituents above, and $R^{1'}$, $R^{2'}$ and $R^{3'}$ independently of one another are as defined for $R^1$, $R^2$ and $R^3$, with the proviso that olefinically unsaturated constituents in $R^1$, $R^2$ and $R^3$ can form the corresponding saturated constituents, nitro can form amino, CO can form CHOH or $CH_2$ and cyano can form aminomethyl, which is characterized in that the hydrogenation is carried out at from 50 to 180° C. and from 1 bar to 400 bar in a reaction system consisting of two liquid, immiscible phases in which elemental hydrogen is dispersed, the first phase being formed by the aromatic compound and, if necessary, a water-immiscible solvent, and the second phase consisting of water, and, colloidally dispersed therein, a hydrogenation-active metal from groups Ib and VIII of the Periodic Table of the Elements (Mendeleev) as hydrogenation catalyst, and auxiliaries for stabilizing the colloidal catalyst, and in the presence of from 100 to 2000% of the stoichiometrically necessary amount of hydrogen.

Examples of straight-chain or branched $C_1$–$C_{18}$-alkyl are methyl, ethyl, propyl, isopropyl, butyl isobutyl, the isomeric pentyls, hexyls, heptyls, octyls, decyls, dodecyls, hexadecyls and octadecyls. Straight-chain or branched $C_2$–$C_{18}$-alkenyl is derived from the corresponding alkyl such that an olefinic double bond is present; it may be internal or terminal. Straight-chain or branched $C_1$–$C_{18}$-alkoxy is derived from the corresponding alkyl such that the alkyl is bonded via an ether oxygen atom.

In preferred terms, alkyl and alkoxy have from 1 to 12 carbon atoms and alkenyl has from 2 to 12 carbon atoms. In particularly preferred terms, alkyl and alkoxy have from 1 to 4 carbon atoms; with particular preference, alkenyl has from 2 to 4 carbon atoms.

Examples of cycloalkyl are cyclopropyl, cyclobutyl, cyclopentyl, methyl-cyclopentyl, dimethyl-cyclopentyl, cyclohexyl, methyl-cyclohexyl, dimethyl-cyclohexyl, cycloheptyl or cyclooctyl. Cycloalkyl is preferably cyclopropyl, cyclopentyl or cyclohexyl.

The group $C_0$–$C_4$-alkanediyl is a spacer group and is accordingly divalent. It may, however, degenerate to a single bond, which is characterized by the expression $C_0$ (no carbon atoms). By complete analogy, the group $C_0$–$C_4$-alkyl is the alcoholic moiety of an ester group, where in the case of $C_0$ the ester group degenerates to the acid hydrogen atom (no carbon atoms). The group —($C_0$–$C_4$-alkanediyl)-COO—($C_0$–$C_4$-alkyl) can thus be the nonesterified carboxyl group —COOH if the two bracketed terms contain $C_0$. Where both brackets contain $C_4$, this is the butyl ester of valeric acid bonded to the ring of the aromatic compound (I). The homologous substituents in between are known to the person skilled in the art.

The group —($C_2$–$C_4$-alkenediyl)-COO—($C_0$–$C_4$-alkyl) includes, for example, in the case of $C_2$-alkenediyl, cinnamic acid or its esters; other homologues of this group are known to the person skilled in the art.

Individual substituents of the group —($C_0$–$C_4$-alkanediyl)-($C_6$–$C_{12}$-aryl) include, in the case of $C_0$, nonspaced aryl substituents, such as phenyl, naphthyl or binapthylyl, and, for example for the case of $C_1$, benzyl, for the case of $C_2$, β-phenylethyl etc. The groups —O—($C_6$–$C_{12}$-aryl) and —S—($C_6$–$C_{12}$-aryl) include, for example, phenoxy, naphthyloxy, biphenyloxy and the corresponding thio analogues.

The substituents $R^1$, $R^2$ and $R^3$ can also be the primary or secondary amino groups containing alkyl or aryl radicals indicated individually.

$R^1$, $R^2$ and $R^3$ can also be phenyl- or alkylphosphine or the phosphine oxide derivable therefrom.

The aryl constituents present in the substituents can also be mono- or disubstituted by $C_1$–$C_4$-alkyl, $C_1$–$C_4$-alkoxy, amino, nitro, hydroxyl or mixtures thereof.

In the case of the abovementioned fused systems, naphthalene (benzo-fused) is obtained as aromatic compound, and in an analogous manner, the indane system, tetrahydronaphthalene system or indene system. These fused moieties which lead to the said systems may also be substituted like the abovementioned aryl constituents.

The substituents of the six-membered ring carbocycle (II), namely $R^{1'}$, $R^{2'}$ and $R^{3'}$, differ from $R^1$, $R^2$ and $R^3$ merely in that substituents which are also hydrogenated at the same time during hydrogenation of the aromatic ring are converted into the correspondingly hydrogenated species. For example, olefinically unsaturated moieties can be converted into the corresponding saturated moieties; thus, for example, cinnamic acid can be converted into β-phenylpropionic acid. In addition, a nitro group can be converted into the amino group, a carbonyl group into a methylene group and the cyano group into aminomethyl. In the case of the conversion of a nitro group into an amino group or where an amino group is already present, the ring hydrogenation and the hydrogenation of the nitro group which takes place simultaneously may be accompanied by another reaction at the amino group and the formation of dicyclohexylamine. This reaction can take place in a known manner via intermediates, for example via cyclohexenylamine, cyclohexylimine or N-phenyl-cyclohexylamine. Such intermediates and their further reaction are known to the person skilled in the art.

Preferably, aromatic compounds of the formula

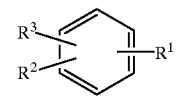

(III)

are used, in which $R^1$, $R^2$ and $R^3$ independently of one another are hydrogen, straight-chain or branched $C_1$–$C_{18}$-alkyl, $C_3$-, $C_5$- or $C_6$-cycloalkyl, straight-chain or branched $C_1$–$C_{18}$-alkoxy, amino, nitro, hydroxyl, —($C_0$–$C_4$-alkanediyl)-COO—($C_0$–$C_4$-alkyl), —CH═CH—COO—($C_0$–$C_4$-alkyl), —($C_0$–$C_4$-alkanediyl)-phenyl, —O-phenyl, —S-phenyl, —NH—($C_1$–$C_{18}$-alkyl), —N($C_1$–$C_{18}$-alkyl)($C_1$–$C_4$-alkyl), —NH-phenyl or —N-(phenyl)($C_1$–$C_4$-alkyl), it being possible for the phenyl constituents to be mono- or disubstituted by $C_1$–$C_4$-alkyl, $C_1$–$C_4$-alkoxy, amino, nitro, hydroxyl or mixtures thereof, and where in addition two of the radicals $R^1$, $R^2$ and $R^3$, if they are adjacent, can, together with the radical of a fused benzene system, be trimethylene or tetramethylene, each of which may be substituted like the above phenyl constituents.

Particularly preferably, in the process according to the invention, aromatic compounds of the formula

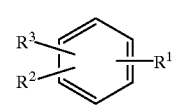

(IV)

are used, in which $R^1$ is as defined above, $R^2$ is hydrogen, $C_1$–$C_4$-alkyl, $C_1$–$C_4$-alkoxy, amino, nitro or hydroxyl, and $R^3$ is hydrogen, $C_1$–$C_4$-alkyl or $C_1$–$C_4$-alkoxy, where in addition the radicals $R^2$ and $R^3$, if they are adjacent, can, together with the radical of a fused benzene system, be trimethylene or tetramethylene, each of which can be substituted like the phenyl constituents of $R^1$.

Examples of aromatic compounds which can be used according to the invention are: benzene, toluene, xylene, ethylbenzene, palmitylbenzene, stearylbenene, cumene, cyclopropyl-benzene, cyclohexyl-benzene, styrene, butenylbenzene, dodecenylbenzene, anisole, phenyl ethyl ether, phenyl butyl ether, phenyl stearyl ether, aniline, phenylenediamine, nitrobenzene, dinitrotoluene, phenol, resorcinol, pyrocatechol, fluorobenzene, difluorobenzene, trifluorobenzene, benzonitrile, dicyanobenzene, benzoic acid, methyl benzoate, butyl benzoate, phenylacetic acid, methyl phenylacetate, β-phenyl-propionic acid, methyl β-phenyl-propionate, cinnamic acid, methyl cinnamate, butyl cinnamate, biphenyl, diphenylmethane, 1,2-diphenyl-ethane, 2,2-diphenyl-propane, bisphenol A, benzophenone, acetophenone, phenyl acetate, phenyl propionate, phenyl butyrate, diphenyl ether, naphthyl phenyl ether, diphenyl thioether, N-methyl-aniline, N-ethyl-aniline, N-stearyl-aniline, N-stearyl-N-methylaniline, diphenylamine, N-naphthyl-aniline, N-methyl-diphenylamine, triphenylphosphine, triphenylphosphine oxide, diphenyl-methylphosphine, phenyl-methyl-phosphine, diphenylmethyl-phospine oxide, phenyl-methyl-phosphine oxide (or its tautomeric form $C_6H_5$—P($CH_3$)—OH), phenyl-di-piperidinophosphine, phenyl-di-methoxy-phosphine oxide, P-phenyl-1-phospha-2,5-dioxa-cyclopentane, 2,4-dinitro-toluene, 4,4'-diamino-diphenyl-methane, 2,6-dinitro-toluene and 2,4'-diamino-diphenyl-methane.

These six-membered ring carbocycles formed therefrom are known to the person skilled in the art and, in. the light of the explanations given above, can be classified unambiguously.

The process according to the invention is characterized by the fact that it is carried out in a reaction system consisting of two liquid, immiscible phases. The first of these two phases is formed by the aromatic compound to be hydrogenated mixed with the carbocyclic compound formed in the course of the reaction. Consequently, it is primarily liquid aromatic compounds that are suitable for the process according to the invention, in turn forming liquid six-membered ring carbocycles. The process according to the invention is, however, also suitable for solid aromatic compounds if a suitable hydrogenation-inert solvent is used. Solvents which can be used for this purpose should be immiscible or only negligibly miscible with the second, essentially aqueous phase. Suitable solvents of this type are, for example, $C_5$–$C_{12}$-alkanes or $C_5$–$C_8$-cycloalkanes, such as pentane, cyclopentane, hexane, cyclohexane, petroleum ether, benzine fractions and other hydrocarbon mixtures. Other suitable solvents are higher alcohols having, from 5 to 10 carbon atoms which have only limited miscibility with water, such as the straight-chain or branched pentanols, hexanols, octanols or decanols.

Other suitable solvents are $CO_2$, which, under the conditions according to the invention, can also be in the supercritical state, ethers, such as diisopropyl ether, tetrahydrofuran or dioxane, and also halogenoalkanes, such as methylene chloride or dichloroethane or perfluorinated or >90% fluorinated alkanes. Where such solvents are used, their amount is from 10 to 1000% by weight, based on the weight of the aromatic compound to be hydrogenated, preferably from 20 to 500% by weight.

The second phase of the reaction system essentially consists of water and, colloidally dispersed therein, hydrogenation-active metal as hydrogenation catalyst. The second phase also comprises substances which are suitable for stabilizing the colloidally dispersed hydrogenation-active metal.

Hydrogenation-active metals which are suitable for the process according to the invention and can be dispersed colloidally are, for example, those from groups Ib and VIII of the Periodic Table of the Elements (Mendeleev).

Examples of specific representatives which may be mentioned are: silver, gold, nickel, palladium, ruthenium, rhodium, platinum, iridium, preferably palladium, ruthenium, rhodium, platinum and nickel. These metals can either be used individually or as a mixture of two or more thereof. Preferred mixtures are Pd/Ru, Pd/Rh, Ni/Ru and Ni/Rh. In the case of such two-component mixtures, the weight ratio of the metals present therein is from 99:1 to 1:99. The hydrogenation-active metals, individually or as a mixture, are present in the overall reaction system in amounts such that at the start of the reaction from 50 to 5000 mol of the aromatic compound to be hydrogenated are present per g-atom of the hydrogenation-active metal. In a further embodiment of the process according to the invention, from 1 to 50 atom-% of the hydrogenation-active metal can be replaced by tin in elemental or ionic form.

The process according to the invention is carried out at a temperature of from 50 to 100° C., preferably from 60 to 80° C., and a pressure of 1 to 400 bar, preferably from 10 to 400 bar, and in particular from 20 to 150 bar. The pressure above the reaction system is maintained by the elemental hydrogen which is present or by a mixture of hydrogen and an inert gas; such inert gases are, for example, nitrogen, argon, neon or a mixture of two or more thereof. In each case, the amount of hydrogen present is from 100 to 2000% of the amount of $H_2$ stoichiometrically required for the above-described hydrogenation, preferably from 150 to 1500%, particularly preferably from 200 to 1000%.

For stabilization of the colloidally dispersed hydrogenation-active metals in the aqueous phase, this aqueous phase additionally comprises stabilizers, such as surfactants from the group consisting of ionic and cationic surfactants, amphiphilic surfactants, such as betaines and sulfobentaines, and amphiphilic sugar surfactants, and nonionic surfactants, such as polyalkylene ethers, including fatty alcohols and monoesterified carbohydrates. Such surfactants are known to the person skilled in the art.

Other additives are basic salts, e.g. LiOH, $Li_2CO_3$, NaOH, Na acetate, potassium phosphate, sodium hydrogenphosphate and the like.

The process according to the invention can be carried out batchwise or continuously. The batchwise procedure involves adding hydrogen or an $H_2$/inert gas mixture under the chosen reaction pressure to the reaction mixture, which consists of the first phase (organic phase with the substrate) and the second phase (aqueous phase with the colloidally dispersed metal), in an autoclave with a mixing or stirring device under oxygen-free conditions, and heating the mixture to the chosen reaction temperature. Hydrogen can be topped up at the same rate as it is consumed; alternatively the reaction can be started at an increased hydrogen pressure and the reaction finished when no further drop in pressure is observed, the pressure being maintained in the pressure range given above. By mixing or stirring the two phases of the reaction system, the hydrogenation hydrogen present is dispersed therein. In the continuous procedure, the two liquid phases can be passed in counter- or concurrent in a suitable reactor, e.g in a tubular reactor, overflow stirred tank reactor or battery of tank reactors, hydrogen which has been added at one or more sites likewise being dispersed. When the reaction is complete, the two phases are separated, for example by simply allowing them to settle. The organic phase is subjected to customary separation measures, such as distillation, crystallisation or preparative chromatography, to isolate the product and to recover any starting material which has not completely reacted. The aqueous phase with the colloidally dispersed metallic hydrogenation catalyst present therein can be recycled to a further batch of the process according to the invention.

The invention is further described in the following illustrative examples. All parts and percentages are by weight, unless otherwise noted.

EXAMPLES

I. Preparation of Hydrogenation-active Colloids

Example 1

887 mg of $PdCl_2$ (5 mmol), 0.37 g of $Li_2CO_3$ (5 mmol) and 6.71 g of sulfobetain of the formula $C_{12}H_{25}N^+(CH_3)_2(CH_2)_3SO_3^-$ (SB12, 20 mmol) were stirred in 0.1 l of water, which had been freed from $O_2$, for 3 hours at room temperature while hydrogen was passed in. A black solution formed. The water was removed from the solution on a rotary evaporator, to give a black wax. After one week in air, this wax was still completely soluble in water. Electron microscopy showed a very finely dispersed colloid. At a stronger magnification, the primary particles from 2 to 5 nm in size could be seen; the atomic ratio for Pd:Cl:S was ≈1:0.4:2.

Example 2

546 mg of $NiBr_2$ (2.5 mmol), 0.185 g of $Li_2CO_3$ (2.5 mmol) and 3.36 g of SB12 as in Example 1 (10.5 mmol) were suspended in 100 ml of $O_2$-free water. Hydrogen was passed in over the course of an hour, which resulted in a colour change from yellow to pale green. 56.7 mg of $NaBH_4$ (1.5 mmol) were added in portions. The solution then turned black within one minute with vigorous foaming. This solution was left to react further for 2 hours with stirring and an aliquot was used for the hydrogenation.

Example 3

0.56 g of Pd acetate (2.5 mmol) was introduced into 10 ml of toluene. 0.35 ml of concentrated $HNO_3$ (5 mmol) was added thereto. After 1 hour, most of the toluene was removed on a rotary evaporator. The residue was taken up in 100 ml of water (saturated with argon); 666 mg of $RhCl_3$ (2.5 mmol) and 6.71 g of a sulfobenaine as in Example 1, but only with a $C_8$-alkyl chain on the N atom (SB8), were added thereto. 0.19 g of $NaBH_4$ was added in portions to this solution; to complete the reaction, the mixture was stirred for a further 3 hours. Electron miscroscopy showed a network of highly compacted centres and paler agglomerate regions (Rh:Pd atomic ratio ≅1 in both regions). At greater magnification primary particles could be seen in the crosslinked region.

Example 4

0.56 g of Pd acetate (2.5 mmol) was stirred for 1 hour in 10 ml of toluene containing 0.35 ml of concentrated $HNO_3$ (5 mmol). Most of the toluene was then removed on a rotary evaporator. The residue was taken up in 100 ml of water (saturated with argon), and 666 mg of $RhCl_3$ (2.5 mmol) and 6 g of polyoxyethylene lauryl ether (5 mmol) were added. 0.19 g of $NaBH_4$ was added in portions. To complete the reaction, the mixture was stirred for a further 3 hours, giving a black solution.

Example 5

444 mg of $PdCl_2$ (2.5 mmol), 654 mg of $RuCl_3$ (2.5 mmol), 369 mg of $Li_2CO_3$ (5 mmol) and 6.71 g of the sulfobetain from Example 1 (20 mmol) were stirred into 100 ml of water (saturated with argon) at room temperature under a hydrogen atmosphere. This gave a black soltuion which, when filtered, produced only a very small amount of sediment. Electron miscroscopy showed a network of highly compacted centres (both Ru:Pd≈2, and Ru:Pd≈0.3) and paler agglomerate regions (Ru:Pd≈1). At greater magnification, the primary particles having dimensions of from 4 to 5 nm and a Ru:Pd atomic ratio ≈1 could easily be seen, as however could many trillings having dimensions of from 10 to 20 nm.

II. Hydrogenations

Example 6

36 ml of isopropylbenzene (cumene) and 25.8 ml of the colloidal solution from Example 5 (0.05 mol/l, 1.29 mmol) were stirred in a 0.1 l stainless steel autoclave for 15 hours at 150° C. and 60 bar of $H_2$. The GCMS (EI) showed 99.5% of isopropyl-cyclohexane.

Example 7

36 ml of cumene and 25.8 ml of the catalyst sol used in Example 6 were stirred in a 0.1 l stainless steel autoclave for 15 minutes at 100° C. and 60 bar of $H_2$. After the pressure had been released, the organic phase was diluted with methylene chloride and separated off. Both $^1$H-NMR and GCMS (EI) showed 100% of formed isopropyl-cyclohexane. 36 ml of cumene were added to the aqueous phase which had been separated off, and the mixture was stirred for 15 hours at 100° C. and 60 bar of $H_2$. After the pressure had been released, the organic phase was diluted with methylene chloride and separated off. The $^1$H-NMR spectrum again showed 100% of isopropyl-cyclohexane.

Example 8

22.9 ml of benzene and 25.6 ml of the catalyst sol used in Example 6 (0.05 mol/l, 1.29 mmol) were stirred in a 0.1 l stainless steel autoclave for 15 hours at 100° C. and 60 bar of $H_2$. After the pressure had been released and the mixture had been decanted, cyclohexane having a purity of 99.89% (GC) was obtained. 97.4% of the aqueous phase was recovered.

Example 9

5.1 g of 4,4'-diamino-diphenylmethane were dissolved in 25 ml of 1-pentanol. 5.12 ml of the catalyst sol as in Example 5 were added thereto, and the reaction mixture was hydrogenated in a 0.1 l autoclave for 15 hours at 100° C. and 60 bar of $H_2$. At 100% conversion, 4,4'-diamino-biscyclohexylmethane was obtained with a selectivity of 32.1% and only partially ring-hydrogenated 4-(4'-amino-cyclohexyl)-aniline with a selectivity of 12.4%. Evidently as a result of $NH_2$—OH exchange because of the presence of water, 4-amino-4'-hydroxy-biscyclohexyl (45.3% selectivity) and 4-(4'-hydroxy-cyclohexyl)-aniline (4.2% selectivity) were also found. The remainder to 100% selectivity consisted of byproducts.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing a 6-membered ring carbocycle comprising ring hydrogenating an aromatic compound in a reaction system comprising a first phase and a second phase that form two liquid, immiscible phases in which elemental hydrogen is dispersed, the hydrogenation occurring in the presence of from 100 to 2000% of the stoichometrically necessary amount of hydrogen, and the hydrogenation of the aromatic compound being carried out at from 50 to 180° C. and from 1 bar to 400 bar;

wherein the first phase is formed by the aromatic compound and the second phase is formed by (i) water, (ii)

a hydrogenation catalyst including a hydrogenation-active metal colloidally dispersed therein which comprises a component selected from compounds consisting of groups Ib and VIII of the Periodic Table of the Elements (Mendeleev), and (iii) auxiliaries for stabilizing the colloidal catalyst.

2. Process of claim 1 wherein the 6-membered ring carbocycles have the formula (II) by ring hydrogenation of aromatic compounds of the formula (I)

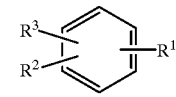
(I)

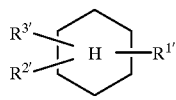
(II)

where, in the formulae, $R^1$, $R^2$ and $R^3$ independently of one another are hydrogen, straight-chain or branched $C_1$–$C_{18}$-alkyl, straight-chain or branched $C_2$–$C_{18}$-alkenyl, $C_3$–$C_8$-cycloalkyl, straight-chain or branched $C_1$–$C_{18}$-alkoxy, amino, nitro, hydroxyl, fluoro, cyano, —($C_0$–$C_4$-alkanediyl)-COO—($C_0$–$C_4$-alkyl), —($C_2$–$C_4$-alkenediyl)-COO—($C_0$–$C_4$-alkyl), —($C_0$–$C_4$-alkanediyl)-$C_6$–$C_{12}$-aryl), —O—CO—($C_1$–$C_{18}$-alkyl), —O—($C_6$–$C_{12}$-aryl), —CO—($C_1$–$C_{18}$-alkyl), CO—($C_6$–$C_{12}$-aryl), —S—($C_6$–$C_{12}$-aryl), —NH—($C_1$–$C_{18}$-alkyl), —N($C_1$–$C_{18}$alkyl)($C_1$–$C_4$-alkyl), —NH—($C_6$–$C_{12}$-aryl), —N($C_6$–$C_{12}$-aryl)($C_1$–$C_4$-alkyl) or —P(X)$_m$(Y)$_n$(Z)$_q$(=O)$_r$, where X, Y and Z independently of one another are phenyl or $C_1$–$C_4$-alkyl, and Y and Z additionally and independently of one another may be OR$^4$ or NR$^4_2$, where R$^4$ is phenyl, $C_1$–$C_4$-alkoxy or $C_1$–$C_4$-alkyl, and NR$^4_2$ can also be piperidino, and Y and Z together can also be —O—CH$_2$CH$_2$—O—, and the bracketed term represents double-bonded oxygen, m is zero, one or two, and n, q and r independently of one another are zero or one, the sum m+n+q+r corresponding to the valency of phosphorus, where aryl constituents may be mono- or disubstituted by $C_1$–$C_4$-alkyl, $C_1$–$C_4$-alkoxy, amino, nitro, hydroxyl or mixtures thereof, and where in addition two of the radicals $R^1$, $R^2$ and $R^3$, if they are adjacent, can together be the radical of a fused benzene or 1,2-naphthalene or 2,3-naphthalene system, trimethylene, tetramethylene or propenediyl, each of which may be substituted like the aryl constituents above, and $R^{1'}$, $R^{2'}$ and $R^{3'}$ independently of one another are as defined for $R^1$, $R^2$ and $R^3$, with the proviso that olefinically unsaturated constituents in $R^1$, $R^2$ and $R^3$ can form the corresponding saturated constituents, nitro can form amino, CO can form CHOH or CH$_2$ and cyano can form aminomethyl.

3. Process according to claim 1, wherein the aromatic compounds of the formula

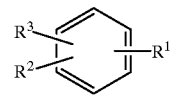
(III)

are used, in which $R^1$, $R^2$ and $R^3$ independently of one another are hydrogen, straight-chain or branched $C_1$–$C_{18}$-alkyl, $C_3$-, $C_5$- or $C_6$-cycloalkyl, straight-chain or branched $C_1$–$C_{18}$-alkoxy, amino, nitro, hydroxyl, —($C_0$–$C_4$-alkanediyl)COO—($C_0$–$C_4$-alkyl), —CH═CH—COO—($C_0$–$C_4$-alkyl), —($C_0$–$C_4$-alkanediyl)-phenyl, —O-phenyl, —S-phenyl, —NH—($C_1$–$C_{18}$-alkyl), —N($C_1$–$C_{18}$alkyl)($C_1$–$C_4$-alkyl), —NH-phenyl or —N-(phenyl)($C_1$–$C_4$-alkyl), it being possible for the phenyl constituents to be mono- or di-substituted by $C_1$–$C_4$-alkyl, $C_1$–$C_4$-alkoxy, amino, nitro, hydroxyl or mixtures thereof, and where in addition two of the radicals $R^1$, $R^2$ and $R^3$, if they are adjacent, can, together with the radical of a fused benzene system, be trimethylene or tetramethylene, each of which may be substituted like the above phenyl constituents.

4. Process according to claim 3, wherein the aromatic compounds of

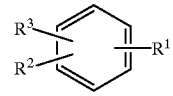
(IV)

are used, in which $R^1$ is as defined in claim 2, $R^2$ is hydrogen, $C_1$–$C_4$-alkyl, $C_1$–$C_4$-alkoxy, amino, nitro or hydroxyl, and $R^3$ is hydrogen, $C_1$–$C_4$-alkyl or $C_1$–$C_4$-alkoxy, where in addition the radicals $R^2$ and $R^3$, if they are adjacent, may, together with the radical of a fused benzene system, be trimethylene or tetramethylene, each of which can be substituted like the phenyl constituents of $R^{11}$.

5. Process according to claim 1, wherein the hydrogenation is carried out at from 60 to 80° C.

6. Process according to claim 1, wherein the hydrogenation is carried out at a pressure of from 10 to 400 bar.

7. Process according to claim 1, wherein the process is carried out in the presence of from 150 to 1500%.

8. Process according to claim 1, wherein the colloidally dispersed metal as hydrogenation catalyst is a metal component comprising a component selected from the group consisting of Pd, Ru, Rh, Pt, Ni, Pd/Ru, Pd/Rh, Ni/Ru and Ni/Rh.

9. Process according to claim 1, wherein from 1 to 50 atom-% of the hydrogenation-active metal is replaced by tin in metallic or ionic form.

10. Process according to claim 1, wherein a solvent is required to form the first phase with the aromatic compound to be hydrogenated, the solvent comprising a component selected from the group consisting of $C_5$–$C_{12}$ alkanes, $C_5$–$C_8$-cycloalkanes, $C_5$–$C_{10}$-alkanols, CO$_2$, open-chain and cyclic $C_4$–$C_8$-ethers and methylene chloride, wherein the solvent is used in an amount of from 10 to 1000% by weight, based on the weight of the aromatic compound.

11. Process according to claim 10, wherein the amount of solvent used is from 20 to 500% by weight, based on the weight of the aromatic compound.

12. The process according to claim 1, wherein the hydrogenation is carried out at a pressure ranging from 20 to 150 bar.

13. The process according to claim 1, wherein the process is carried out in the presence of from 200 to 1000%, of the amount of hydrogen stoichiometrically required for the hydrogenation.

* * * * *